United States Patent [19]

Adelstein et al.

[11] 4,072,686
[45] Feb. 7, 1978

[54] 1-(3,3,3-TRIARYLALKYL)-4-PHENYL-PIPERIDINEALKANOLS

[75] Inventors: Gilbert W. Adelstein, Evanston; Esam Z. Dajani, Buffalo Grove; Chung Hwai Yen, Skokie, all of Ill.

[73] Assignee: G. D. Searle & Co., Chicago, Ill.

[21] Appl. No.: 733,502

[22] Filed: Oct. 18, 1976

Related U.S. Application Data

[63] Continuation-in-part of Ser. No. 568,439, April 16, 1975, Pat. No. 3,998,832.

[30] Foreign Application Priority Data

Mar. 18, 1976 South Africa ............... 76/1681

[51] Int. Cl.$^2$ .................. C07D 401/06; C07D 211/22
[52] U.S. Cl. ............... 260/293.69; 260/293.81; 260/293.83; 260/293.84; 424/263; 424/267; 260/293.77
[58] Field of Search ............ 260/293.69, 293.81, 260/293.83, 293.84

[56] References Cited
PUBLICATIONS

Patai et al., "J. Chem. Soc." pp. 716–723 (1962).
Martensson et al., "Acta Chim. Scand." vol. 19, No. 3, pp.711–722 (1965).
Bochow, "Chem. Ber." vol. 108 pp. 3475–3482 (1975).

*Primary Examiner*—Natalie Trousof
*Assistant Examiner*—Robert T. Bond
*Attorney, Agent, or Firm*—John J. McDonnell

[57] ABSTRACT

The present invention encompasses compounds of the formula

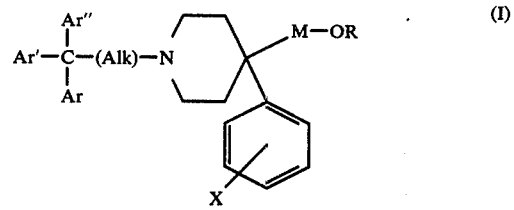

and pharmaceutically acceptable acid addition salts thereof wherein the Alk is straight or branched chain alkylene containing 2-4 carbon atoms; M is alkylene having 1-4 carbon atoms; Ar and Ar' are phenyl, alkyl substituted phenyl wherein the alkyl contains from 1-4 carbon atoms or halo substituted phenyl; Ar" is phenyl, alkyl substituted phenyl wherein the alkyl contains 1-4 carbon atoms, halo substituted phenyl or pyridyl; X is hydrogen, halogen, trifluoromethyl or alkyl having from 1-4 carbon atoms; R is hydrogen alkyl having from 1-7 carbon atoms or an alkanoyl having from 2-5 carbon atoms. These compounds are potent antidiarrheal agents characterized by little, if any, central nervous system activity.

28 Claims, No Drawings

1-(3,3,3-TRIARYLALKYL)-4-PHENYL-PIPERIDINEALKANOLS

This is a continuation-in-part of our copending application Ser. No. 568,439, filed Apr. 16, 1975, now U.S. Pat. No. 3,998,832.

The present invention encompasses a compound of the formula

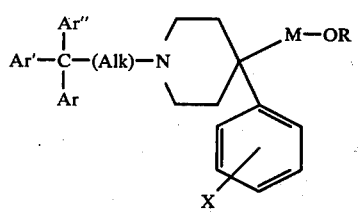

and pharmaceutically acceptable acid addition salts thereof wherein the Alk is straight or branched chain alkylene containing 2-4 carbon atoms; M is alkylene having 1-4 carbon atoms; Ar and Ar' are phenyl, alkyl substituted phenyl wherein the alkyl contains from 1-4 carbon atoms or halo substituted phenyl; Ar" is phenyl, alkyl substituted phenyl wherein the alkyl contains 1-4 carbon atoms, halo substituted phenyl or pyridyl; X is hydrogen, halogen, trifluoromethyl or alkyl having from 1-4 carbon atoms; R is hydrogen alkyl having from 1-7 carbon atoms or an alkanoyl having from 2-5 carbon atoms.

The term Alk represents alkylene exemplified by radicals such as propylene, ethylene, —(CH$_2$)$_n$— where $n$ is 2-4 or propylene. Ethylene is preferred.

M represents straight and branched chain alkylenes of the formula —(C$_n$H$_{2n}$)$_n$— wherein $n$ is 1-4. Methylene —CH$_2$— and ethylene —CH$_2$—CH$_2$— are preferred.

R represents hydrogen; alkyl having 1-7 carbon atoms such as methyl, ethyl, propyl, butyl, pentyl, hexyl, heptyl, and the branched chain isomers thereof; alkanoyl such as acetyl, propionyl, butyryl and isobutyryl; X represents halogen including fluoro, chloro, bromo, iodo; alkyl exemplified by methyl, ethyl, propyl, butyl and the branched chain isomers thereof; or trifluoromethyl.

Ar and Ar' represent phenyl substituted phenyl radicals such as tolyl, ethylphenyl, butylphenyl, chlorophenyl, fluorophenyl, and bromophenyl.

Ar" represents 2, 3, and 4 pyridyl in addition to phenyl and above exemplified substituted phenyl radicals.

The present invention also includes optically active compounds prepared by resolving the above compounds which have assymetric centers.

Compounds of the formula

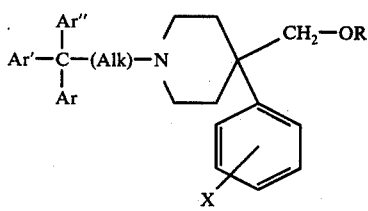

or

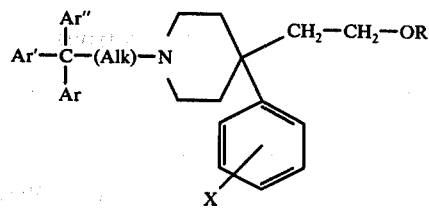

wherein Ar, Ar', Ar", Alk, R and X are as previously described are preferred.

The embodiments wherein Alk is —CH$_2$—CH$_2$— are particularly preferred.

Compounds of the formula

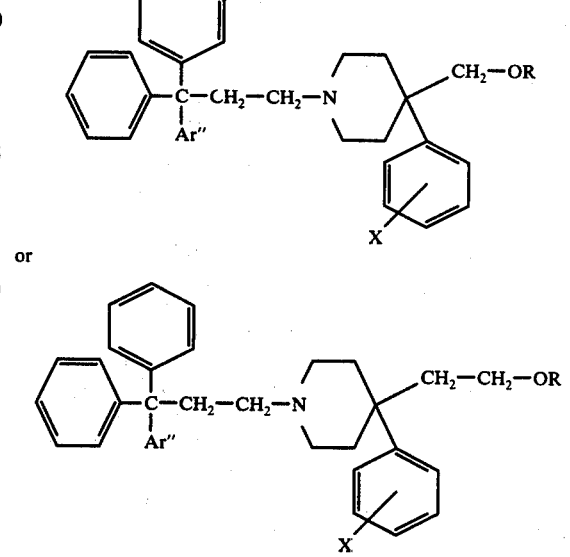

and the pharmaceutically acceptable acid addition salts thereof wherein Ar" is phenyl or pyridyl and X and R are as previously defined are likewise preferred.

Compounds of the formula

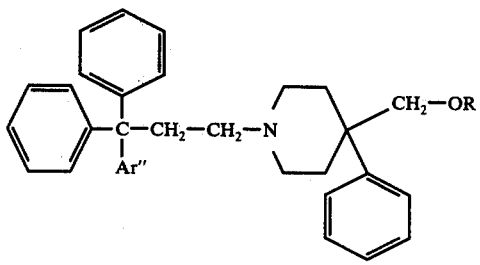

or

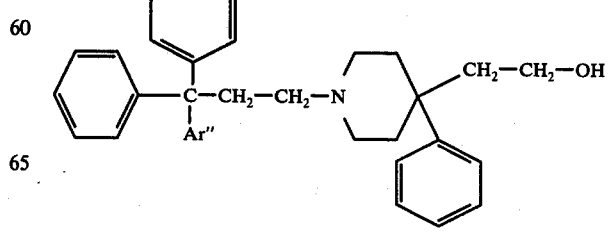

and the pharmaceutically acceptable acid addition salts thereof wherein Ar'' is phenyl or pyridyl are particularly preferred embodiments.

The triphenyl derivatives of the formula

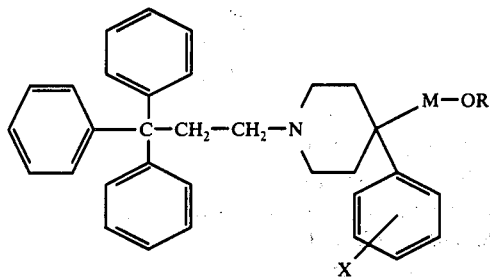

and pyridyl compounds of the formula

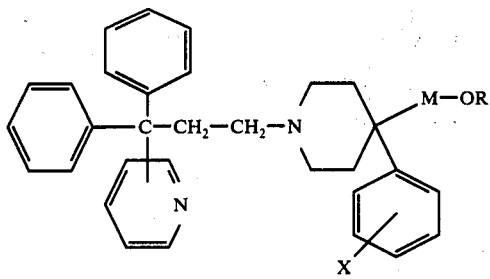

and the pharmaceutically acceptable acid addition salts thereof wherein M, R, and X are as earlier defined.

Equivalent to the compounds of both for the purposes of this invention are the pharmaceutically acceptable acid addition salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Specifically preferred embodiments are
1-(3,3,3-triphenylpropyl)-4-phenyl-4-piperidinemethanol hydrochloride,
1-[3,3,-diphenyl-3-(2-pyridyl)propyl]-4-phenyl-4-piperidinemethanol hydrochloride,
1-(3,3,3-triphenylpropyl)-4-phenyl-4-acetoxymethylpiperidine hydrochloride,
1-(3,3,3-triphenylpropyl)-4-phenyl-4-methoxymethylpiperidine hydrochloride,
1-(3,3,3-triphenylpropyl)-4-(4-chlorophenyl)-4-piperidinemethanol hydrochloride,
1-[3-p-chlorophenyl-3,3-diphenylpropyl]-4-(4-phenyl)-4-piperidinemethanol hydrochloride,
1-[3-(p-tolyl)-3,3-diphenylpropyl]-4-(phenyl)-4-piperidinemethanol hydrochloride,
1-[3-(p-bromophenyl)-3,3-diphenylpropyl]-4-(phenyl)-4-piperidinemethanol hydrochloride,
1-[3,3-diphenyl-3-(4-pyridyl)propyl]-4-phenyl-4-piperidinemethanol hydrochloride,
1-[3,3-diphenyl-3-(3-pyridyl)propyl]-4-phenyl-4-piperidinemethanol hydrochloride,
1-(3,3,3-triphenylpropyl)-4-phenyl-4-hexoxymethylpiperidine hydrochloride,
1-(3,3,3-triphenylpropyl)-4-(p-tolyl)-4-piperidinemethanol hydrochloride,
1-(3,3,3-triphenylpropyl)-4-(p-trifluoromethyl)-4-piperidinemethanol hydrochloride,
1-(4,4,4-triphenylbutyl)-4-(phenyl)-4-piperidinemethanol hydrochloride,
1-(3,3,3-triphenylpropyl)-4-(phenyl)-4-piperidineethanol hydrochloride,
1-(3,3,3-triphenylpropyl)-4-phenyl-4-methoxyethylpiperidine hydrochloride,
1-[3,3-diphenyl-3-(2-pyridyl)propyl]-4-phenyl-4-methoxyethylpiperidine hydrochloride,
1-(3,3,3-triphenylpropyl)-4-phenyl-4-piperidinemethanol,
1-[3,3,-diphenyl-3-(2-pyridyl)propyl]-4-phenyl-4-piperidinemethanol,
1-(3,3,3-triphenylpropyl)-4-phenyl-4-acetoxymethylpiperidine,
1-(3,3,3-triphenylpropyl)-4-phenyl-4-methoxymethylpiperidine,
1-(3,3,3-triphenylpropyl)-4-(chlorophenyl)-4-piperidinemethanol,
1-[3-p-chlorophenyl-3,3-diphenylpropyl]-4-(phenyl)-4-piperidinemethanol,
1-[3-(p-tolyl)-3,3-diphenylpropyl]-4-(phenyl)-4-piperidinemethanol,
1-[3-(p-bromophenyl)-3,3-diphenylpropyl]-4-(phenyl)-4-piperidinemethanol,
1-[3,3-diphenyl-3-(4-pyridyl)propyl]-4-phenyl-4-piperidinemethanol,
1-[3,3-diphenyl-3-(3-pyridyl)propyl]-4-phenyl-4-piperidinemethanol,
1-(3,3,3-triphenylpropyl)-4-phenyl-4-hexoxymethylpiperidine,
1-(3,3,3-triphenylpropyl)-4-(p-tolyl)-4-piperidinemethanol,
1-(3,3,3-triphenylpropyl)-4-(p-trifluoromethyl)-4-piperidinemethanol,
1-(4,4,4-triphenylbutyl)-4-(phenyl)-4-piperidinemethanol,
1-(3,3,3-triphenylpropyl)-4-(phenyl)-4-piperidineethanol,
1-(3,3,3-triphenylpropyl)-4-phenyl-4-methoxyethylpiperidine, and
1-[3,3-diphenyl-3-(2-pyridyl)propyl]-4-phenyl-4-methoxyethylpiperidine.

Compounds of the present invention are prepared by methods set out in Scheme I

SCHEME I

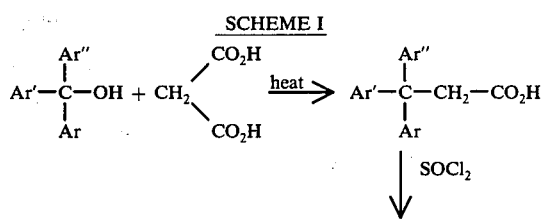

SCHEME I -continued

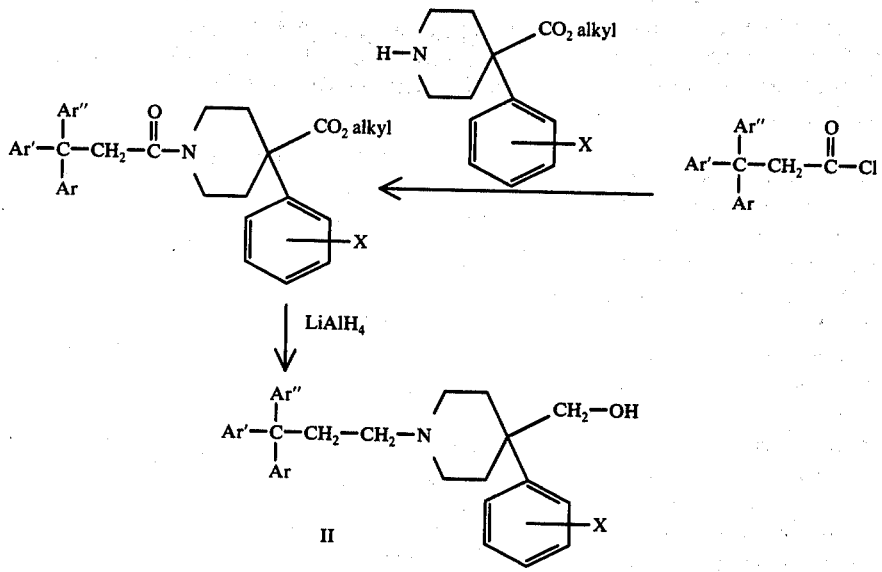

wherein Ar, Ar′, Ar″ and X are as previously defined with the proviso that (a) when the compounds of Formula I in which R is an alkanoyl radical are desired the compounds of Formula II are esterified with a suitable anhydride in a basic medium to give the desired esters of Formula I and (b) when the compounds of Formula I in which R is an alkyl radical are desired the compounds of Formula II can be treated with sodium hydride in a suitable solvent and then further treated with an alkyl halide to give the desired ethers of Formula I.

Reduction of triaryl propionic acid to the corresponding alcohol, treatment of the alcohol with thionyl chloride, followed by formation of the Grinard reagent and carbonation provides chain extended acids wherein Alk can be increased to trimethylene. Reaction with methyl lithium to provide the methyl ketone prior to reduction, chlorination, and carbonation provides (Alk) equal to propylene.

An alternate process for the preparation of the compounds of this invention comprises reacting a compound of the formula

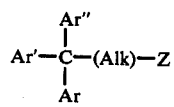

wherein Alk, Ar, Ar′, Ar″ are defined as before and Z is chlorine or bromine with a compound of the general formula

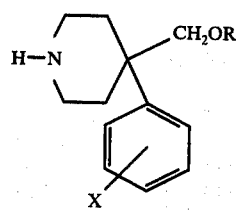

wherein R and X are as defined as before in a suitable inert solvent such as toluene, benzene, methylene chloride, 4-methyl-2-pentanone or cyclohexane in the presence of an acid acceptor such as triethylamine or potassium carbonate to give the compounds of Formula I.

Another process for the preparation of compounds of the present invention wherein R of Formula I is alkyl or alkanoyl comprises reacting a compound of the general formula

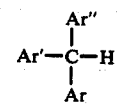

wherein Ar, Ar′ and Ar″ are defined as before with n-butyl lithium in a suitable organic solvent and further reacting this mixture with a compound of the general formula

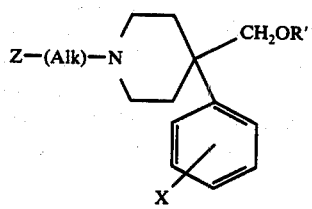

wherein Alk and X are defined as before and Z is chlorine or bromine and R′ is alkyl or alkanoyl to give the compounds of Formula I wherein R is alkyl or alkanoyl.

Useful techniques and intermediates are disclosed by S. Patai and Dayogi, J. Chem Soc 716 (1962), D. Martensson and E. Nilsson, Acta Chem Scand. 19(3) 711 (1965) CA-63-6968h and H. Bochow Chem Ber 108, 3475 (1975). A wide variety of triphenylcarbinols are prepared by the reaction:

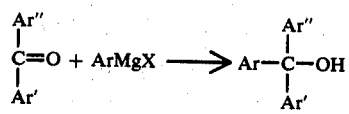

N-(3,3,3-triphenylpropyl)morpholine and N-(3,3,3-triphenylpropyl)piperidine are known compounds, Martensson and Nilsson, Acta Chem Scand 19 (1965) 711–722. Compounds of the present invention are particularly distinct by virtue of R—O—M— and X substituted phenyls in the 4 position of the piperidine ring.

Compounds of the present invention are potent antidiarrheal agents with little, if any, central nervous system activity.

The compounds herein described can be combined with pharmaceutically acceptable carriers to provide novel pharmaceutical compositions. The concentration of active ingredient in the composition is not critical, but is preferably 1–80%. These compositions can be administered orally, suitably forms for such administration including tablets, lozenges, capsules, dragees, pills, powders, solutions, suspensions and syrups. Acceptable pharmaceutical carriers are exemplified by gelatin capsules; sugars such as lactose or sucrose; starches such as corn starch or potato starch; cellulose derivatives such as sodium carboxymethyl cellulose, ethyl cellulose, methyl cellulose, or cellulose acetate phthalate; gelatin; talc; calcium phosphates such as diacalcium phosphate or tricalcium phosphate; sodium sulfate; calcium sulfate; polyvinyl pyrrolidone; acacia; polyvinyl alcohol; stearic acid; alkaline earth metal stearates such as magnesium stearate; oils such as peanut oil, cottonseed oil, sesame oil, olive oil, corn oil, oil of theobroma; water; agar; alginic acid; and benzyl alcohol, as well as other non-toxic compatible substances used in pharmaceutical formulations.

The compounds of this invention can be used to produce an antidiarrheal effect in mammals by administering the instant novel compositions containing a therapeutically effective amount of the active ingredient. The term "therapeutically effective amount" is defined as the amount of active ingredient that will produce an antidiarrheal effect, i.e. which will reverse, inhibit or prevent diarrhea. For a particular subject, the amount of active ingredient to be used will vary with the subject involved, the severity of the diarrhea, and the particular active ingredient used. The therapeutically effective amount of a particularly active ingredient is determined by comparing its potency to that of a known standard such as diphenoxylate HCl(Cutting's Handbook of Pharmacology 4th edition, Appleton-Century Crafts, N.Y. at page 642.

CASTOR OIL INDUCED DIARRHEA IN THE RAT

Adult Charles River male rats were fasted in community cages for 24 hours prior to the test, with free access to water. The compound was administered intragastrically (suspended on 0.5% methylcellulose) one hour prior to the administration of castor oil at the dose of 1.0 ml/rat intragastrically. The rats were then observed for the presence or absence of diarrhea, at hourly intervals for up to 8 hours past administration of castor oil. The median effective dose values at each hourly interval were calculated for the compound using the method of Berkson (1953). When tested in the above procedures 1-(3,3,3-triphenylpropyl)-4-phenyl-4-piperidinemethanol was found to be very active in its ability to inhibit gastrointestinal motility. For example:

Comparative Oral Antidiarrheal Potency and Duration of 1-(3,3,3-triphenylpropyl)-4-phenyl-4-piperidinemethanol hydrochloride (a) to Diphenoxylate hydrochloride in the Rat Castor Oil Diarrhea Test

| Treatment | $ED_{50}\pm$ S.E. in mg/kg at Hourly Intervals After Castor Oil | | | | | | |
|---|---|---|---|---|---|---|---|
| | 2 | 3 | 4 | 5 | 6 | 7 | 8 |
| Diphenoxylate | 0.22 | 0.36 | 0.71 | 1.21 | 1.62 | 1.85 | 1.93 |
| S.E. | 0.04 | 0.11 | 0.14 | 0.20 | 0.28 | 0.28 | 0.32 |
| Potency | 1.0 | 1.0 | 1.0 | 1.0 | 1.0 | 1.0 | 1.0 |
| (a) | 0.14 | 0.18 | 0.24 | 0.28 | 0.28 | 0.28 | 0.35 |
| S.E. | 0.03 | 0.04 | 0.05 | 0.05 | 0.05 | 0.05 | 0.08 |
| Potency | 1.35 | 2.25 | 3.25 | 4.33 | 5.71 | 6.44 | 5.42 |

The assessment of the analgesic effect of the instant compounds was conducted in the mouse hot plate and tail clip tests.

MOUSE HOT PLATE TEST

A mouse (adult male weighing 18–25 grams) is placed in a restraining cylinder on a hot plate with the temperature controlled at 55° ± 0.3° C. The reaction time of the mouse to lick a foot or jump is measured at 60, 40 and 20 minutes before and 30, 60, 90 and 120 minutes after administration of the test compound. The "normal" reaction time is measured as the median of the three pretreatment reaction times. A positive response consists of a reaction time greater than twice the normal time at any of the post treatment times. A dose of the test compound is considered active when 50 percent or more of the animals used show a positive response.

CHARCOAL MEAL TEST

Mice weighing 18–24 grams and previously fasted for 24 hours are each given orally 0.2 ml. of a suspension containing 10% charcoal and 1% methylcellulose. The test compounds are administered intragastrically one hour prior to the charcoal meal. 3.5 Hours after administration of the meal the mice are sacrificed by cervical dislocation and the cecum is examined for the presence or absence of charcoal on an all-or-none basis. Each compound is tested at three dose levels (typically 30, 10, 3 mg/kg) in groups of 6 mice per dose level. Control groups of mice given vehicle only were run concurrently with each test group.

TAIL CLIP TEST

A special clip is applied to the base of the tail of the mouse (adult male weighing 18–25 grams) and the time for the animal to turn around to bite as it is measured. The sensitivity of each mouse is determined one-half hour prior to drug administration. Only those mice attempting to bite the clip are included in the experiment. The test compound is then administered intragastrically and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response. Then tested in the above procedures 1-(3,3,3-triphenylpropyl)-4-phenyl-4-piperidinemethanol showed very little analgesic effect.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth temperatures are given in degress Centigrade (° C), and relative amounts in parts by weight, except as otherwise noted.

EXAMPLE 1

A mixture of 2 parts of triphenylcarbinol and 8 parts of malonic acid are heated at 170° for 31 hours. This mixture is cooled and then dissolved in hot ethanol. 3,3,3-Triphenylpropionic acid, melting at 182°, crystallizes from the ethanol upon cooling. 1 Part of 3,3,3-triphenylpropionic acid is then refluxed with 5 parts of thionyl chloride for 4 hours and the excess thionyl chloride is removed in vacuum to provide the crude 3,3,3-triphenylpropionyl chloride. 9 Parts of this 3,3,3-triphenylpropionyl chloride are then reacted with 27.0 parts of ethyl 4-phenyl-4-piperidinecarboxylate in the presence of 4 parts of triethylamine in benzene. The resulting amide is reduced with 5 parts of lithium aluminum hydride in ether at reflux for 2.5 hours. The reaction mixture is cooled and treated with 15% aqueous sodium hydroxide solution to decompose any unreacted lithium aluminum hydride. The reaction mixture is then filtered and washed with ether. The ether solution is evaporated to give an oil. This oil is then slurried in 10% HCl and extracted with ether. The aqueous phase which contains an insoluble oil is extracted with methylene chloride, and the methylene chloride extract dried over anhydrous sodium sulfate. Evaporation of this methylene chloride solution gives a solid which is taken up in acetone and precipitated with ether to give 1-(3,3,3-triphenylpropyl)-4-(phenyl)-4-piperidinemethanol hydrochloride, melting at about 256°-259° C.

This compound has the following structural formula

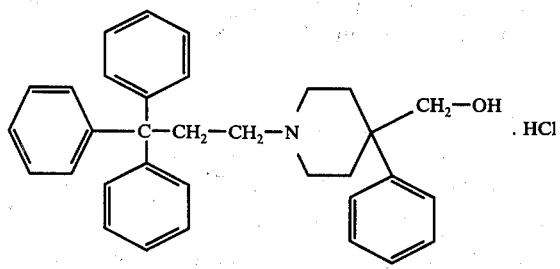

Substitution of 2 parts of (p-chlorophenyl) diphenyl methanol for the triphenylcarbinol used above and substantial repetition of the foregoing procedure affords 1-[3-(p-chlorophenyl)-3,3-diphenylpropyl]-4-(phenyl)-4-piperidinemethanol hydrochloride having the following structural formula

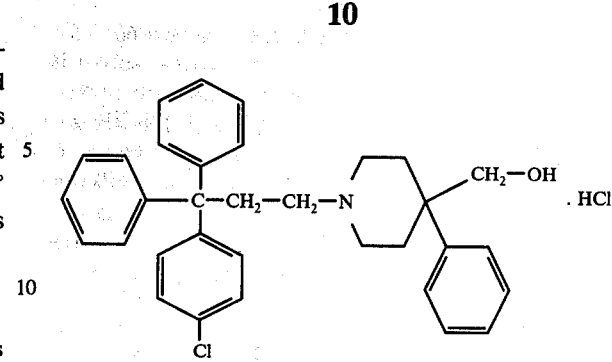

Substitution of 2 parts of 1,1-diphenyl-1-(p-tolyl)methanol for the triphenylcarbinol used above and substantial repetition of the foregoing procedure affords 1-[3-(p-tolyl)-3,3-diphenylpropyl]-4-(phenyl)-4-piperidinemethanol hydrochloride.

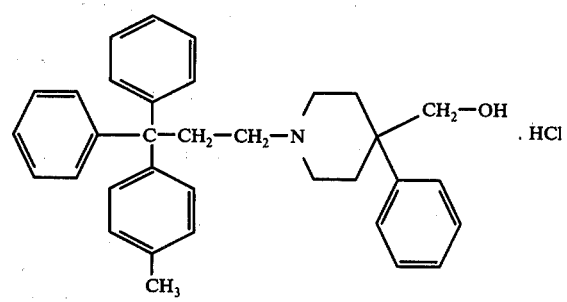

Substitution of 2 parts of (p-bromophenyl)diphenylmethanol for the triphenylcarbinol used above and substantial repetition of the foregoing procedure affords 1-[3-(p-bromophenyl)-3,3-diphenylpropyl]-4-(phenyl)-4-piperidinemethanol hydrochloride.

Substitution of 2 parts of 1,1-diphenyl-1-(p-n-butylphenyl)methanol for the triphenylcarbinol used above and substantial repetition of the foregoing procedure affords 1-[3-(n-butylphenyl)-3,3-diphenylpropyl]-4-(phenyl)-4-piperidinemethanol hydrochloride.

A mixture of 1.7 parts of 3,3,3-triphenylpropyl-chloride, 0.49 part of 4-phenyl-4-piperidinemethanol hydrochloride, 0.46 part of potassium carbonate, 0.17 part of potassium iodide, 1 part of water and 3.2 parts of 4-methyl-2-pentanone is refluxed for 2 hours. The solvent is then evaporated and the residue is partitioned between methylene chloride and water. The organic layer is separated, washed with water and with saturated aqueous sodium chloride solution and then dried over sodium sulfate. Evaporation of the solvent leaves a semi-solid residue which is slurried in ether and then filtered to remove the solid. The solvent is evaporated from the filtrate leaving an oily residue which is taken up in refluxing hexane. The hexane solution is then decanted and cooled and the oily solid which forms is removed by filtration. Evaporation of the solvent from the filtrate gives 1-(3,3,3-triphenylpropyl)-4-(4-phenyl)-4-piperidinemethanol. Reaction of this free base with aqueous oxalic acid solution and crystallization provides 1-(3,3,3-triphenylpropyl)-4-(4-phenyl)-4-piperidinemethanol oxalate.

EXAMPLE 2

A mixture of 9.9 parts of ethyl 4-phenyl-4-piperidinecarboxylic, 41.8 parts of 4-methyl-2-pentanone, 4.3 parts of ethylene oxide and 79.2 parts of ethanol is heated in a sealed citric bottle at about 60° C for 7 days. The resulting solution is cooled, the solvent is evaporated under reduced pressure and the residual material is partitioned between diluted NaOH and ether. The ether layer is then separated and extracted with diluted HCl. The acid layer is then made alkaline with aqueous sodium hydroxide and the resulting mixture is extracted with ether. The ether layer is dried over sodium sulfate and potassium carbonate and evaporated in vacuum. The residue is crystallized from ether-n-pentane to give 1-(2-hydroxyethyl)-4-phenyl-4-piperidinecarboxylic acid ethyl ester melting at about 91.5°–93° C.

A solution is prepared from 5.9 parts of the ester obtained in the preceding paragraph and 134 parts of methylene chloride. This solution is saturated with hydrogen chloride gas at below 10° and 5.1 parts of thionyl chloride is added. The mixture is refluxed for 1 hour and then cooled and volatile material is removed under reduced pressure. The residue is dissolved in 88 parts of benzene, and the solution evaporated under reduced pressure. The residue is then crystallized from a mixture of ethanol and ether to give 1-(2-chloroethyl)-4-phenyl-4-piperidinecarboxylic acid ethyl ester hydrochloride melting at about 216°–218°.

To a solution of 4.4 parts of diphenyl-2-pyridylmethane in 50 parts of cyclohexane is added under nitrogen 8.8 parts by volume of a 2.17 molar solution of butyllithium in hexane. This solution is stirred at room temperature for 1.5 hours and than a solution of ethyl 1-(2-chloroethyl)-4-phenyl-4-piperidinecarboxylate, obtained from 6.0 parts of the corresponding hydrochloric salt, in 27 parts of cyclohexane is added and the mixture is refluxed with stirring for 4 hours. The mixture is cooled, diluted with 71 parts of ether and then washed with water. The organic layer is then extracted with dilute HCl resulting in the precipitation of gum. The aqueous layer is separated from the gum and the organic layer washed with ether, made strongly alkaline with aqueous NaOH liberating brown-red oil, and extracted with ether. The ether extract is dried (Na$_2$SO$_4$) and evaporated under reduced pressure giving a brown-red gum. This gum is redissolved in ether, treated with Darco, filtered, concentrated and diluted with n-pentane for crystallization. This gives ethyl 1-[3,3-diphenyl-3-(2-pyridyl)propyl]-4-phenyl-4-piperidinecarboxylate melting at about 125°–128°. ED$_{50}$ 2 hrs. post castor oil = 0.04 mpk and weak analgesia (mouse tail clip test) at 100 and 30 mpk.

A mixture of 2.9 parts of this ester and 0.66 part of lithium aluminum hydride in 177 parts of ether is heated and stirred under nitrogen for 2.5 hours. Additional 0.66 part of lithium aluminum hydride is added. The mixture is refluxed and stirred for 2 hours and then decomposed by the successive addition of 1.4 parts of water, 1.0 parts by volume of 20% sodium hydroxide solution, and 4.8 parts of water. The mixture is filtered and the solvent is evaporated to 4–10 ml to allow crystallization. This crude product is recrystallized from ether giving 1-[3,3-diphenyl-3-(2-pyridyl)propyl]-4-phenyl-4-piperidinemethanol melting at about 148°–151° C having the following structural formula

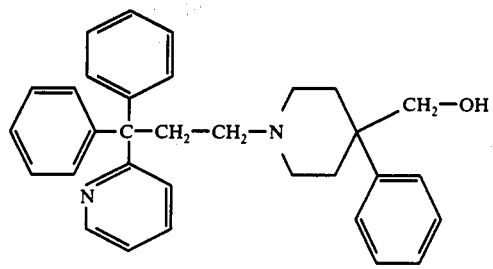

Following the above procedure using 4.4 parts of diphenyl-4-pyridylmethane provides 1-[3,3-diphenyl-3-(4-pyridyl)propyl]-4-phenyl-4-piperidinemethanol having the formula

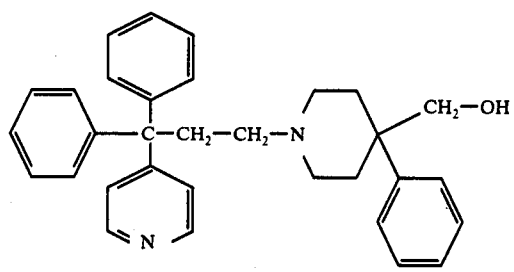

Substituting diphenyl-3-pyridylmethane provides 1-[3,3-diphenyl-3-(3-pyridyl)propyl]-4-phenyl-4-piperidinemethanol.

EXAMPLE 3

A mixture of 1.0 part of 1-(3,3,3-triphenylpropyl)-4-phenyl-4-piperidinemethanol hydrochloride, 10 parts by volume of pyridine and 3.0 parts by volume of acetic anhydride is allowed to stand for 24 hours. Volatile material is removed under reduced pressure and the resulting residue is partitioned between dilute sodium hydroxide and ether. The ether layer is separated, washed with water, dried over sodium sulfate and then treated with an excess of a solution of hydrogen chloride in 2-propanol. The solid which forms is separated by filtration and then washed successively with ether, water, and ether, and then air dried to give 1-(3,3,3-triphenylpropyl)-4-phenyl-4-acetoxymethylpiperidine hydrochloride melting at about 211°–213° C and having the following structural formula

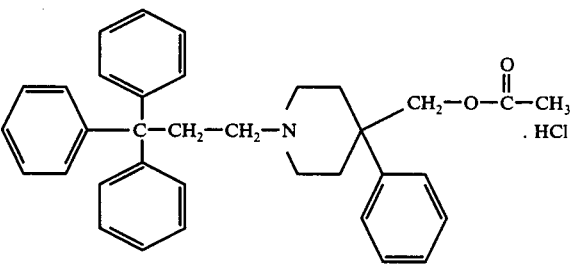

Replacement of acetic anhydride with 3.0 parts of propionic acid anhydride provides 1-(3,3,3-triphenylpropyl)-4-phenyl-4-propionyloxymethylpiperidine hydrochloride.

EXAMPLE 4

A solution of 3.0 parts of 1-(3,3,3-triphenylpropyl)-4-phenyl-4-piperidinemethanol (obtained from the corresponding hydrochloride salt), 0.35 part of 50% sodium hydride suspension in mineral oil, and 70 parts by volume of 1,2-dimethoxyethane are heated at 37°–39° C for 1.5 hours under nitrogen with stirring. The mixture is cooled to room temperature and 0.94 part of methyl iodide is added and the mixture is stirred at room temperature for 20 hours. The solvent is evaporated under reduced pressure and the residue is suspended in ether and filtered. The filtrate is washed with water, dried (Na$_2$SO$_4$) and evaporated under reduced pressure. The residue is put on an 0.5 inch column of Woelm silica gel and eluted with 2% ethanol in benzene under a pressure which maintains a flow rate of 8 ml/minute. The desired eluate evaporates and the residue dissolves in ether and is treated with an excess of hydrogen chloride in 2-propanol. The solid which forms is separated by filtration, washed with ether, and air dried and then further recrystallized from a mixture of methanol and ether to give 1-(3,3,3-triphenylpropyl)-4-phenyl-4-methoxymethylpiperidine hydrochloride melting at about 212°–213.5° C having the following structural formula

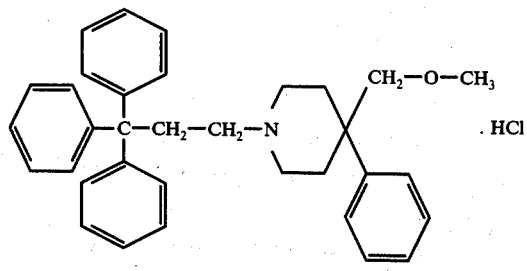

Following the above procedure using an equivalent quantity of n-hexylbromide in place of methyl iodide provides 1-(3,3,3-triphenylpropyl)-4-phenyl-4-hexoxymethylpiperidine hydrochloride melting at 152°–155° C and having the following structural formula

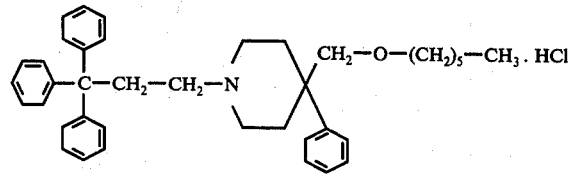

Following the above procedure using equivalent quantities of ethylbromide in place of methyliodide provides 1-(3,3,3-triphenylpropyl)-4-phenyl-4-ethoxymethylpiperidine hydrochloride.

Substituting equivalent quantities of 1-[3,3-diphenyl-3-(2-pyridyl)propyl]-4-phenyl-4-piperidinemethanol for 1-(3,3,3-triphenylpropyl)-4-phenyl-4-piperidinemethanol and ethyl bromide for methyliodide in the above procedure provides 1-[3,3-diphenyl-3-(2-pyridyl)propyl]-4-phenyl-4-ethoxymethylpiperidine hydrochloride having the formula

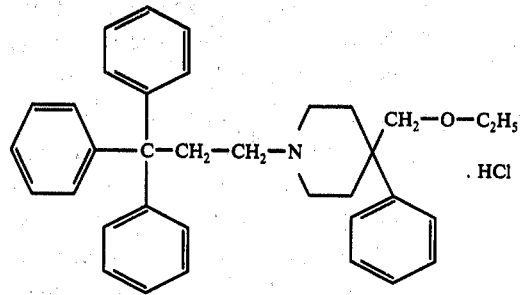

EXAMPLE 5

A mixture of 63.7 parts of bis-2-chloroethylamine hydrochloride, 67.8 parts of 4-toluenesulphonyl chloride and 955 parts of methylene chloride is cooled in an ice bath and then 356 parts by volume of a 2N aqueous sodium hydroxide solution is added with stirring at 5°–8° C. The mixture is stirred at 5°–8° C for 3 hours and then at room temperature for 18 hours. The organic layer is separated and washed successively with dilute hydrochloric acid, water, dilute potassium carbonate solution, and water and then dried over sodium sulfate. The solvent is then evaporated under reduced pressure and the residual oil is crystallized from methanol go give N,N-bis(2-chloroethyl)-4-toluenesulfonamide malting at about 45°–47° C.

To a solution of 60.3 parts of 4-chlorophenylacetonitrile and 118 parts of N,N-bis(2-chloroethyl)-4-toluenesulfonamide in 720 parts of dried benzene under N$_2$ there is added portionwise with stirring at 10°–13° C 32.6 parts of sodamide. The cooling bath is then removed and the mixture is stirred for one hour during which time the temperature rises to 70° C and then falls back to 43° C. Ice cold water is added to the mixture and a fine solid forms. This is separated by filtration and washed successively with water and benzene and dried and then triturated in boiling methanol. The undissolved solid is separated by filtration, washed with water and dried to give 1-(4-toluenesulfonyl)-4-(4-chlorophenyl)-4-piperidinecarbonitrile melting at about 202°–206° C.

The nitrile obtained in the preceding paragraph (37.5 parts) is added to 45.5 parts of 75% sulfuric acid with stirring. The resulting paste is heated to 140°–150° C with stirring for 1.5 hours. The mixture is then cooled and 120 parts of anhydrous ethanol is added. The mixture is then distilled until the pot temperature reaches 125° C. Addition of ethanol and distillation is repeated twice before the mixture is finally heated to 150° C and then cooled to room temperature. It is than poured into ice water containing excess sodium hydroxide. The mixture is then extracted with ether and the ether extract is dried and concentrated. It is then cooled to 0° C and filtered to remove solid material. The filtrate is then distilled to give a liquid boiling at 120°–125° C at 0.1 mm pressure. The distillate is then dissolved in 50 parts by volume of n-pentane and cooled to low temperature (−70° C) whereupon a gummy precipitate forms and the remaining liquid is removed by decantation; this is repeated 4 times and finally the gum solidifies. The solid is washed with cold pentane and then dried under reduced pressure to give 4-(4-chlorophenyl)-4-piperidinecarboxylic acid ethyl ester (an oil at room temperature).

A solution of 3.3 parts of 3,3,3-triphenylpropionic acid in 108 parts of dry benzene is treated with 1.8 parts of thionyl chloride. The mixture is refluxed for 2 hours before it is cooled and volatile material is removed under reduced pressure. The residue is dissolved in 88 parts of dry benzene and the solvent is removed again under reduced pressure to again give a residual oil. This is again dissolved in 88 parts of dry benzene and a solution of 2.9 parts of 4-(4-chlorophenyl)-4-piperidinecarboxylic acid ethyl ester and 1.1 part of triethylamine in 27 parts of dry benzene is added at 15°-25° C with stirring. The mixture is then allowed to stand for 16 hours before it is washed successively with dilute hydrochloric acid, water, and dilute aqueous potassium carbonate solution. It is then dried over sodium sulfate and the solvent is evaporated under reduced pressure to leave a residual gum. Upon trituration with pentane the gum solidifies and it is filtered, washed with pentane and air dried to give 1-(3,3,3-triphenylpropionyl)-4-(4-chlorophenyl)-4-piperidinecarboxylic acid ethyl ester melting at about 95°-98° C. 3.8 Patts of this compound is continuously extracted into a suspension of 1.1 part of lithium aluminum hydride in ether with stirring at reflux under nitrogen over a period of one hour. Stirring is continued for an additional 50 minutes and the mixture is decomposed by the successive addition of 1.1 part of water, 0.8 part of 20% aqueous sodium hydroxide solution and 3.9 parts of water. The mixture is filtered and the inorganic material is extracted woth ether. The combined ether solutions are concentrated and diluted with pentane. The solid material which forms is separated by filtration, washed with a mixture of ether and pentane, and dried under reduced pressure to give 1-(3,3,3-triphenylpropyl)-4-(4-chlorophenyl)-4-piperidinemethanol melting at about 156.5°-157.5° C and having the following structural formula

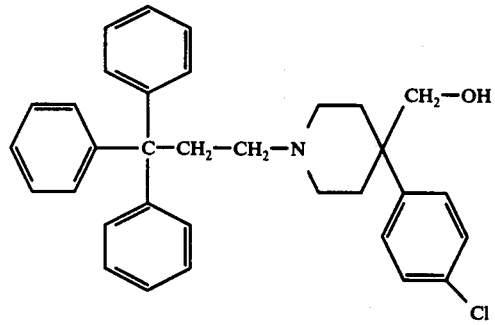

Substitution of p-tolylacetonitrile for 4-chlorophenylacetonitrile used above and substantial repetition of the foregoing procedure provides 1-(3,3,3-triphenylpropyl)-4-(p-tolyl)-4-piperidinemethanol having the following structural formula

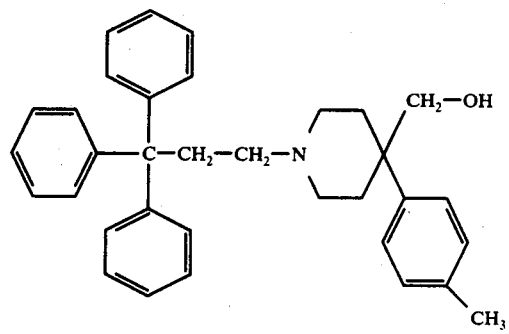

Substitution of 4-ethylphenylacetonitrile for 4-chlorophenylacetonitrile used avove and substantial repetition of the foregoing procedure provides 1-(3,3,3-triphenylpropyl)-4-(p-ethylphenyl)-4-piperidinemethanol having the formula

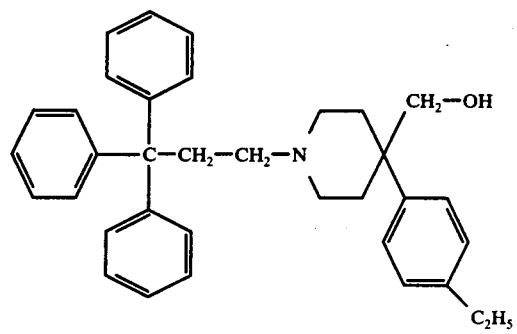

Substitution of p-fluorophenylacetonitrile for 4-chlorophenylacetonitrile used above and substantial repetition of the foregoing procedure provides 1-(3,3,3-triphenylpropyl)-4-(p-fluorophenyl)-4-piperidinemethanol having the formula

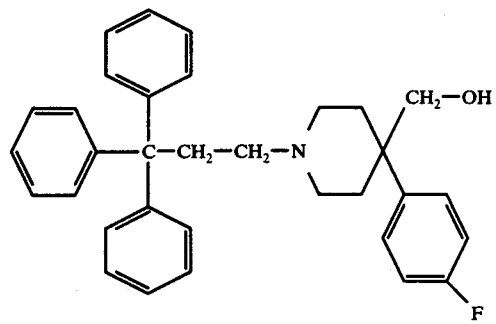

Substitution of p-trifluoromethylacetonitrile for 4-chlorophenylacetonitrile used above and substantial repetition of the foregoing procedure provides 1-(3,3,3-triphenylpropyl)-4-(p-trifluoromethylphenyl)-4-piperidinemethanol having the following structural formula

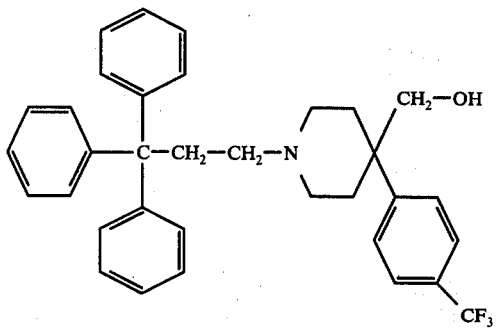

EXAMPLE 6

4,4,4-Triphenylbutyronitrile is hydrolized by standard procedure to give 4,4,4-triphenylbutyric acid. Substitution of 4,4,4-triphenylbutyric acid for the 3,3,3-triphenylpropionic acid of Example 1 and substantial repetition of the procedure of Example I affords 1-(4,4,4-triphenylbutyl)-4-(phenyl)-4-piperidinemethanol having the following structural formula

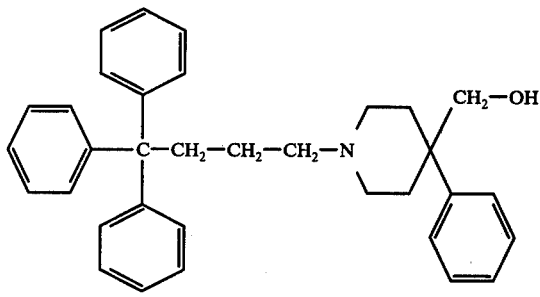

EXAMPLE 7

9 Parts of 3,3,3-triphenylpropionyl chloride is reacted with 27 parts of 4-phenyl-4-piperidine ethanol prepared by the method of H. Bochow and W. Schneider, Chem Ber 108, 3475 (1975) are reacted according to the procedure in Example 1 and the resulting amide is reduced with lithium aluminum hydride to provide 1-(3,3,3-triphenylpropyl)-4-(4-phenyl)-4-piperidineethanol having the following formula

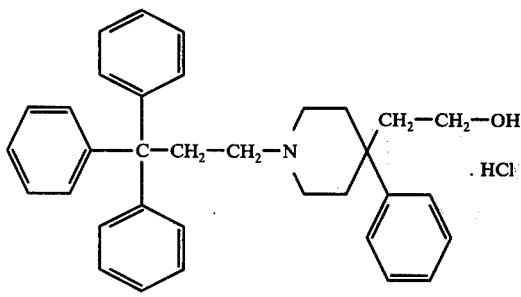

Alternatively this compound is prepared by the reaction of 4-phenyl-4-piperidineethanol with 3,3,3-triphenylpropyl chloride, also as described in Example 1. Reaction with acetic anhydride by methods set out in Example 3 provides 1-(3,3,3-triphenylpropyl)-4-phenyl-4-acetoxyethylpiperidine hydrochloride.

1-(3,3,3-Triphenylpropyl)-4-phenyl-4-methoxyethyl-piperidine hydrochloride is made by the methods set out in Example 4. That compound has the following formula

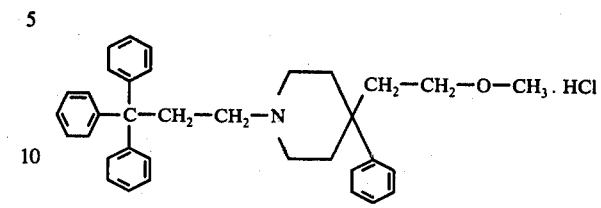

EXAMPLE 8

7 Parts of 1-p-toluenesulfonyl-4-hydroxyethyl-4-phenylpiperidine, prepared by the method of H. Bochow and W. Schneider, Chem Ber 108, 3475 (1975), is allowed to react with 3 parts of dimethylsulfate in dilute sodium hydroxide solution to give 1-p-toluenesulfonyl-4-methoxyethyl-4-phenylpiperidine. The resulting ether is refluxed in 6N HCl and the resulting amine is allowed to react with ethylene oxide in methanol go give 1-hydroxyethyl-4-methoxyethyl-4-phenylpiperidine. 2 Parts of the latter compound and 1 part of thionylchloride react to give 1-chloroethyl-4-methoxyethyl-4-phenylpiperidine hydrochloride. A solution of 2.2 parts of the free base of the latter compound in THF is reacted with the lithium salt of diphenyl-2-pyridyl methane (prepared from 2.4 parts of diphenyl-2-pyridyl methane and 1 part of n-butyl lithium in THF). The resulting compound is 1-[3,3-diphenyl-3(2-pyridyl)-propyl]-4-phenyl-4-methoxyethylpiperidine; hydrochloride is isolated as described in earlier procedures and has the formula

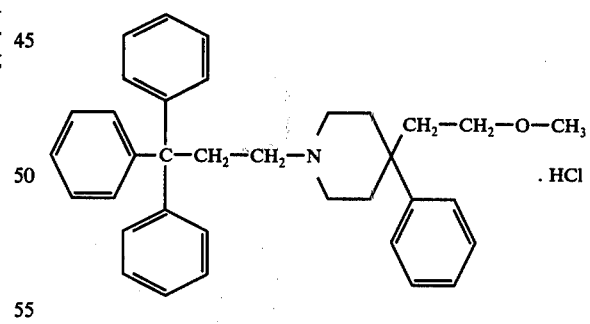

EXAMPLE 9

Following the procedure in Example 4 and using equivalent quantities of 1-[3,3-diphenyl-3-(2-pyridyl)-propyl]-4-phenyl-4-piperidinemethanol is converted to 1-[3,3-diphenyl-3-(2-pyridyl)propyl]-4-phenyl-4-methoxymethylpiperidine hydrochloride or the free base 1-[3,3-diphenyl-3-(2-pyridyl)propyl]-4-phenyl-4-methoxymethylpiperidine melting at 129.5°– 131.5° C and having the formula

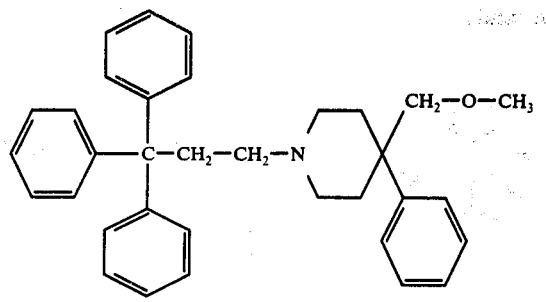

What we claim is:
1. A compound of the formula

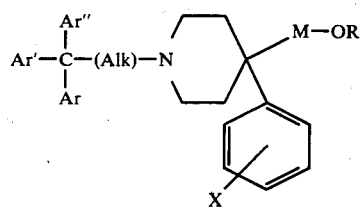

and pharmaceutically acceptable acid addition salts thereof wherein the Alk is straight or branched chain alkylene containing 2–4 carbon atoms; M is alkylene having 1–4 carbon atoms; Ar and Ar' are phenyl, alkyl substituted phenyl wherein the alkyl contains from 1–4 carbon atoms or halo substituted phenyl; Ar" is phenyl, alkyl substituted phenyl wherein the alkyl contains 1–4 carbon atoms, halo substituted phenyl or pyridyl; X is hydrogen, halogen, trifluoromethyl or alkyl having from 1–4 carbon atoms; R is hydrogen, alkyl having from 1–7 carbon atoms or alkanoyl having from 2–5 carbon atoms.

2. A compound according to claim 1 of the formula

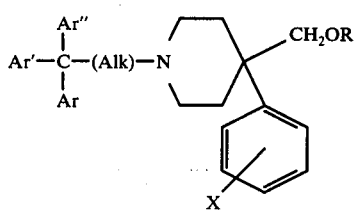

and pharmaceutically acceptable acid addition salts thereof wherein the Alk is straight or branched-chain alkylene containing 2–4 carbon atoms; Ar and Ar' are phenyl, alkyl substituted phenyl wherein the alkyl contains from 1–4 carbon atoms or halo substituted phenyl; Ar" is phenyl, alkyl substituted phenyl wherein the alkyl contains 1–4 carbon atoms, halo substituted phenyl or pyridyl; X is hydrogen, halogen, trifluoromethyl or alkyl having from 1–4 carbon atoms; R is hydrogen, alkyl having from 1–7 carbon atoms or an alkanoyl having from 2–5 carbon atoms.

3. A compound according to claim 1 of the formula

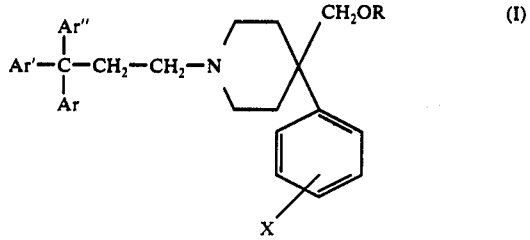

and pharmaceutically acceptable acid addition salts thereof wherein Ar and Ar' are phenyl, alkyl substituted phenyl wherein the alkyl contains from 1–4 carbon atoms or halo substituted phenyl; Ar" is phenyl, alkyl substituted phenyl wherein the alkyl contains 1–4 carbon atoms, halo substituted phenyl or pyridyl; X is hydrogen, halogen, trifluoromethyl or an alkyl having from 1–4 carbon atoms; R is hydrogen, an alkyl having from 1–7 carbon atoms or alkanoyl having from 2–5 carbon atoms.

4. A compound according to claim 1 of the formula

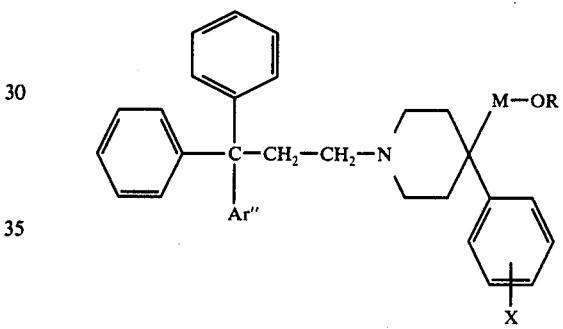

and pharmaceutically acceptable acid addition salts thereof wherein Ar" is phenyl or pyridyl, M is alkylene having 1–4 carbon atoms, R is hydrogen, an alkyl having 1–7 carbon atoms or alkanoyl having from 2–5 carbon atoms, and X is hydrogen, halogen, trifluoromethyl or alkyl having from 1–4 carbon atoms.

5. A compound according to claim 1 of the formula

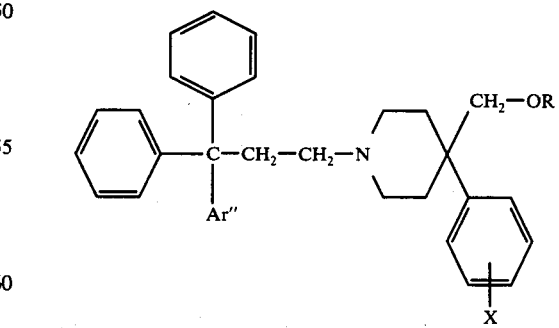

wherein Ar" is phenyl or pyridyl, R is hydrogen, an alkyl having 1–7 carbon atoms or alkanoyl having from 2–5 carbon atoms, and X is hydrogen; halogen, trifluoromethyl or alkyl having from 1–4 carbon atoms.

6. A compound according to claim 1 of the formula

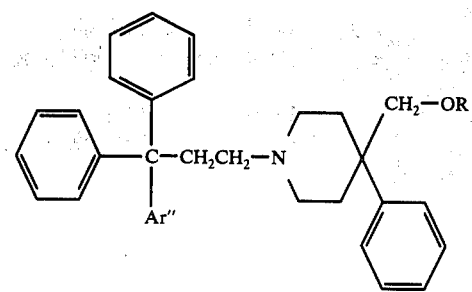

and the pharmaceutically acceptable salts thereof wherein Ar" is phenyl or pyridyl.

7. A compound according to claim 1 of the formula

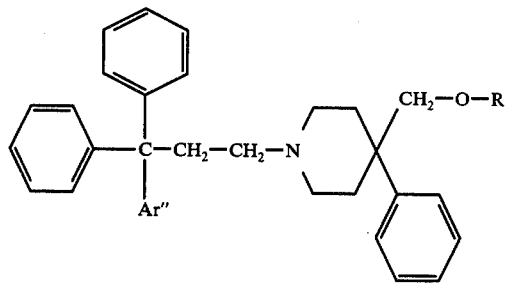

and the pharmaceutically acceptable acid addition salts thereof wherein Ar" is phenyl or pyridyl and R is alkyl having 1–7 carbon atoms.

8. A compound according to claim 1 of the formula

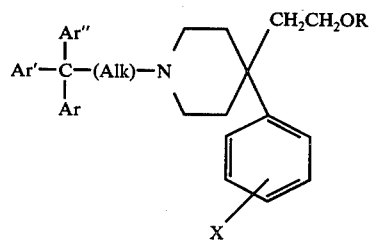 (I)

and pharmaceutically acceptable acid addition salts thereof wherein the Alk is straight or branched chain alkylene containing 2–4 carbon atoms; Ar and Ar' are phenyl, alkyl substituted phenyl wherein the alkyl contains from 1–4 carbon atoms or halo substituted phenyl; Ar" is phenyl, alkyl substituted phenyl wherein the alkyl contains 1–4 carbon atoms, halo substituted ppenyl or pyridyl; X is hydrogen, halogen, trifluoromethyl or alkyl having from 1–4 carbon atoms; R is hydrogen, alkyl having from 1–7 carbon atoms or an alkanoyl having from 2–5 carbon atoms.

9. A compound according to claim 1 of the formula

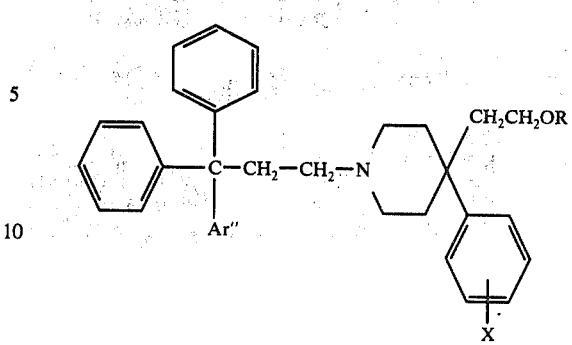

wherein Ar" is phenyl or pyridyl, R is hydrogen, an alkyl having 1–7 carbon atoms or alkanoyl having from 2–5 carbon atoms, and X is hydrogen; halogen, trifluoromethyl or alkyl having from 1–4 carbon atoms.

10. A compound according to claim 1 of the formula

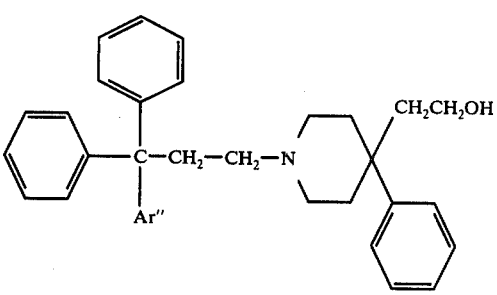

and the pharmaceutically acceptable salts thereof wherein Ar" is phenyl or pyridyl.

11. A compound according to claim 1 which is 1-(3,3,3-triphenylpropyl)-4-phenyl-4-piperidinemethanol.

12. A compound according to claim 1 which is 1-[3,3-diphenyl-3-(2-pyridyl)propyl]-4-phenyl-4-piperidinemethanol.

13. A compound according to claim 1 which is 1-(3,3,3-triphenylpropyl)-4-phenyl-4-acetoxymethyl-piperidine.

14. A compound according to claim 1 which is 1-(3,3,3-triphenylpropyl)-4-phenyl-4-methoxymethyl-piperidine.

15. A compound according to claim 1 which is 1-(3,3,3-triphenylpropyl)-4-(4-chlorophenyl)-4-piperidinemethanol.

16. A compound according to claim 1 which is 1-[3-p-chlorophenyl-3,3-diphenylpropyl]-4-(phenyl)-4-piperidine methanol.

17. A compound according to claim 1 which is 1-[3-(p-tolyl)-3,3-diphenylpropyl]-4-(phenyl)-4-piperidinemethanol.

18. A compound according to claim 1 which is 1-[3-(p-bromophenyl)-3,3-diphenylpropyl]-4-(phenyl)-4-piperidinemethanol.

19. A compound according to claim 1 which is 1-[3,3-diphenyl-3-(4-pyridyl)propyl]-4-phenyl-4-piperidinemethanol.

20. A compound according to claim 1 which is 1-[3,3-diphenyl-3-(3-pyridyl)propyl]-4-phenyl-4-piperidinemethanol.

21. A compound according to claim 1 which is 1-(3,3,3-triphenylpropyl)-4-phenyl-4-hexoxymethyl-piperidine.

22. A compound according to claim 1 which is 1-(3,3,3-triphenylpropyl)-4-(p-tolyl)-4-piperidinemethanol.

23. A compound according to claim 1 which is 1-(3,3,3-triphenylpropyl)-4-(p-trifluoromethyl)-4-piperidinemethanol.

24. A compound according to claim 1 which is 1-(4,4,4-triphenylbutyl)-4-(phenyl)-4-piperidinemethanol.

25. A compound according to claim 1 which is 1-(3,3,3-triphenylpropyl)-4-(phenyl)-4-piperidineethanol.

26. A compound according to claim 1 which is 1-(3,3,3-triphenylpropyl)-4-phenyl-4-methoxyethylpiperidine.

27. A compound according to claim 1 which is 1-[3,3-diphenyl-3-(2-pyridyl)propyl]-4-phenyl-4-methoxyethylpiperidine.

28. A compound according to claim 1 which is 1-[3,3-diphenyl-3-(2-pyridyl)propyl]-4-phenyl-4-methoxymethylpiperidine.

* * * * *